US010457668B2

(12) United States Patent
Charyulu et al.

(10) Patent No.: US 10,457,668 B2
(45) Date of Patent: Oct. 29, 2019

(54) CRYSTALLINE FORMS OF POSACONAZOLE INTERMEDIATE AND PROCESS FOR THE PREPARATION OF AMORPHOUS POSACONAZOLE

(71) Applicant: BIOCON LIMITED, Electronic, Karnataka (IN)

(72) Inventors: Palle Venkata Raghavendra Charyulu, Hyderabad (IN); Dharshan Jakkali Chandre Gowda, Mudigere (IN); Shanmughasamy Rajmahendra, Chennai (IN); Manikandan Raman, Hosur (IN)

(73) Assignee: BIOCON LIMITED, Karnataka (IN)

( * ) Notice: Subject to any disclaimer, the term of this patent is extended or adjusted under 35 U.S.C. 154(b) by 0 days.

(21) Appl. No.: 15/762,523

(22) PCT Filed: Sep. 22, 2016

(86) PCT No.: PCT/IB2016/055660
§ 371 (c)(1),
(2) Date: Mar. 22, 2018

(87) PCT Pub. No.: WO2017/051342
PCT Pub. Date: Mar. 30, 2017

(65) Prior Publication Data
US 2018/0319777 A1 Nov. 8, 2018

(30) Foreign Application Priority Data

Sep. 23, 2015 (IN) .......................... 5080/CHE/2015
Nov. 6, 2015 (IN) .......................... 6013/CHE/2015

(51) Int. Cl.
*C07D 405/14* (2006.01)
*B01D 9/00* (2006.01)

(52) U.S. Cl.
CPC .......... *C07D 405/14* (2013.01); *B01D 9/005* (2013.01); *B01D 9/0045* (2013.01); *B01D 9/0063* (2013.01); *B01D 2009/009* (2013.01)

(58) Field of Classification Search
CPC .................................................. C07D 405/14
See application file for complete search history.

(56) References Cited

U.S. PATENT DOCUMENTS

| 5,625,064 | A | * | 4/1997 | Andrews | ............... C07D 231/12 544/366 |
| 5,661,151 | A | * | 8/1997 | Saksena | ............... C07D 231/12 514/227.8 |
| 5,693,626 | A | * | 12/1997 | Saksena | ............... C07D 231/12 514/227.8 |
| 5,703,079 | A | * | 12/1997 | Saksena | ............... C07D 231/12 514/254.07 |
| 5,710,154 | A | * | 1/1998 | Saksena | ............... C07D 231/12 514/227.8 |
| 5,714,490 | A | * | 2/1998 | Saksena | ............... C07D 231/12 514/227.8 |
| 7,834,193 | B2 | | 11/2010 | Yamaguchi et al. | |
| 9,102,664 | B2 | * | 8/2015 | Reddy | .................. C07D 405/14 |
| 2007/0197627 | A1 | | 8/2007 | Yamaguchi et al. | |
| 2016/0237066 | A1 | * | 8/2016 | Thirumalai Rajan | ....................... C07D 405/14 |

FOREIGN PATENT DOCUMENTS

| CN | 101993407 A | 3/2011 |
| CN | 104140389 A | 11/2014 |
| CN | 104370894 A | 2/2015 |
| CN | 106699741 A | * 5/2017 |
| JP | H06-220015 A | 8/1994 |
| JP | 2000-247998 A | 9/2000 |
| JP | 2001-199956 A | 7/2001 |

(Continued)

OTHER PUBLICATIONS

M. Hepperle et al., 43 Tetrahedron Letters, 3359-3363 (2002).*
Solid State Characterization of Pharmaceuticals (R.A. Storey et al., eds., 2011) (Year: 2011).*
International Search Report for International Application No. PCT/IB2016/055660 dated Nov. 28, 2016.
Written Opinion of the International Searching Authority for International Application No. PCT/IB2016/055660 dated Nov. 28, 2016.

*Primary Examiner* — Alexander R Pagano
(74) *Attorney, Agent, or Firm* — Katten Muchin Rosenman LLP

(57) ABSTRACT

The present invention provides an industrial method production of amorphous posaconazole. The present invention also relates to a method for production of the posaconazole via and novel crystalline forms of posaconazole intermediate. More particularly the present invention relates to novel crystalline forms of posaconazole intermediate and methods for production of novel crystalline forms of posaconazole intermediate represented by the following structural formula III Which is key intermediate in the production of posaconazole. The present invention also provides for the one pot process for the preparation of amorphous posaconazole using novel crystalline forms of benzyl posaconazole.

12 Claims, 7 Drawing Sheets

(56) References Cited

FOREIGN PATENT DOCUMENTS

| | | | |
|---|---|---|---|
| JP | 2002-265444 A | 9/2002 | |
| WO | WO-9517407 A1 * | 6/1995 | ........... C07D 231/12 |
| WO | 2009/141837 A2 | 11/2009 | |
| WO | 2011/158248 A2 | 12/2011 | |
| WO | 2013/042138 A2 | 3/2013 | |
| WO | 2015/059716 A2 | 4/2015 | |
| WO | WO-2015059716 A2 * | 4/2015 | ........... C07D 405/14 |
| WO | WO-2017147893 A1 * | 9/2017 | ........... C07D 405/14 |

* cited by examiner

CRYSTALLINE FORMS OF POSACONAZOLE INTERMEDIATE AND PROCESS FOR THE PREPARATION OF AMORPHOUS POSACONAZOLE

RELATED APPLICATION

This application claims the benefit of priority of our Indian patent application numbers 5080/CHE/2015 filed on Sep. 23, 2015 & 6013/CHE/2015 filed on Nov. 6, 2015 which are incorporated herein by reference.

TECHNICAL FIELD

The present invention relates to a method for production of the posaconazole via and novel crystalline forms of posaconazole intermediate. More particularly the present invention relates to novel crystalline forms of posaconazole intermediate and methods for production of novel crystalline forms of posaconazole intermediate represented by the following structural formula

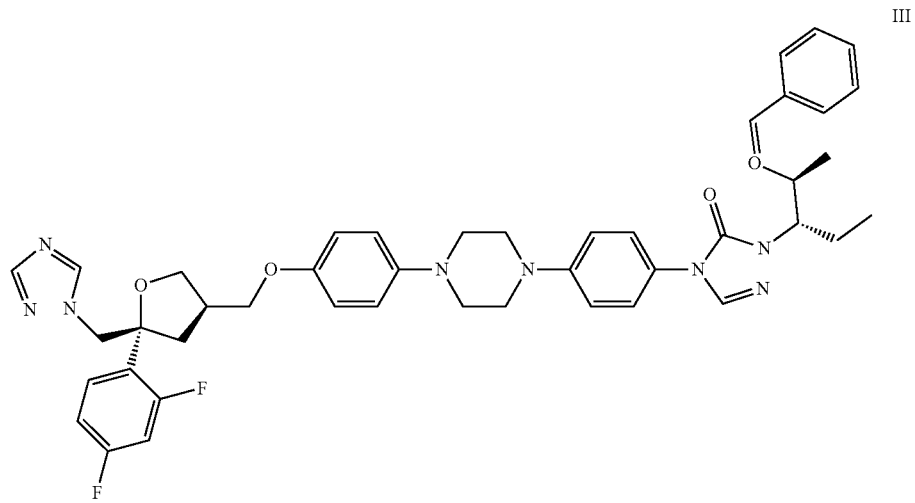

III

Which is key intermediate in the production of posaconazole. Posaconazole commercially known as NOXAFIL is a triazole antifungal agent indicated for prophylaxis of invasive *Aspergillus* and *Candida* infections in patients, 13 years of age and older, who are at high risk of developing these infections due to being severely immunocompromised, such as HSCT recipients with GVHD or those with hematologic malignancies with prolonged neutropenia from chemotherapy. NOXAFIL is also indicated for the treatment of oropharyngeal candidiasis (OPC), including OPC refractory (rOPC) to itraconazole and/or fluconazole.

BACKGROUND AND PRIOR ART OF THE DISCLOSURE

Posaconazole commercially known as NOXAFIL is a triazole antifungal agent indicated for treatment of invasive fungal infections.

As an effective and efficient method for production of posaconazole, it is proposed that the preparation of the intermediate of posaconazole herein after termed as benzyl posaconazole represented by structural formula III:

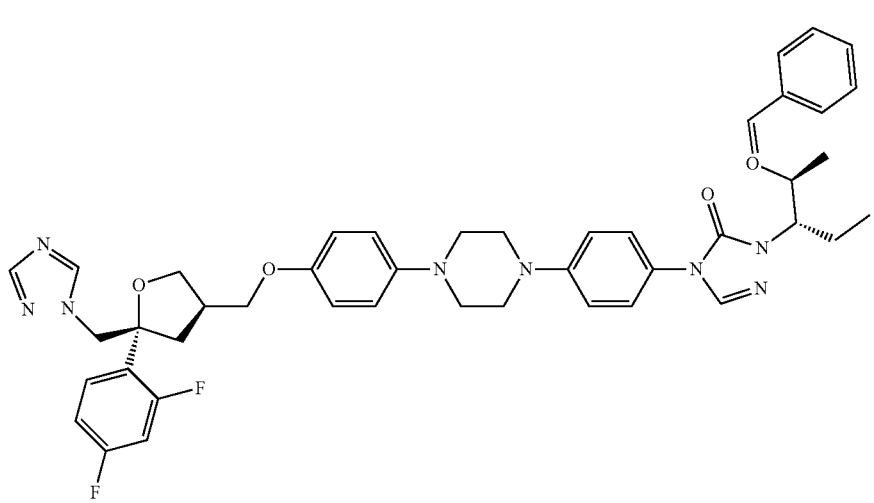

is suitable for a large scale production, the intermediate is crystalline which leads to ready solubility of the crystalline intermediate and overall impacting on the yield of the posaconazole API.

Crystalline forms of benzyl posaconazole are reported earlier. The International patent publication WO2011158248 (A2) claims benzyl posaconazole of Form A, which is characterised by its powder X-ray diffractogram having peaks at about 2.04, 61, 12.24, 15.06, 15.73, 17.17, 17.37, 18.15, 19.42, 19.97, 24.34, 26.0 and the WO2013042138 (A3) claims crystalline benzyl posaconazole of Form M, which is characterised by its powder X-ray diffractogram having peaks at about 3.90, 5.86, 7.82, 9.82, 11.79, 12.59, 13.38, 13.74, 16.24, 16.95, 17.83, 18.90, 20.09, 21.49, 22.89, 24.93, 26.53, 27.56, 28.73, 29.88 and 34.20. In order to achieve a method for higher yields of posaconazole in large scale production it is of necessity to develop new crystalline forms of benzyl posaconazole.

The above need is addressed in the present invention via novel crystalline polymorphs B-1, B-2 & B-3 of Benzyl posaconazole. The novel polymorphs are characterised by powder X-ray diffractogram having peaks as below:

Prominent 2θ values Crystalline form B-1: 4.14, 6.85, 9.92, 15.28, 15.69, 16.59, 17.29, 17.92, 18.27, 18.91, 20.63, 19.95, 23.58, and 25.12±0.2 degrees of 2θ.

Prominent 2θ values Crystalline form B-2: 4.20, 9.27, 14.22, 15.46, 15.82, 16.45, 17.31, 19.09, 20.47, 21.18, and 24.74±0.2 degrees of 2θ

Prominent 2θ values Crystalline form B-3: 7.07, 14.49, 15.68, 16.50, 18.05, 20.13, 20.87, 22.85, and 24.42±0.2 degrees of 2θ

The typical precision of the 2-theta values of crystalline forms B-1, B-2 & B-3 are in the range of about ±0.2 degrees of 2θ.

Patent Reference 1: PCT Publication WO2011158248;
Patent Reference 2: PCT Publication WO2013042138;

The present disclosure aims to provide novel crystalline polymorphic forms of benzyl posaconazole and methods for preparation of the same at industrial scale.

The present disclosure also aims to provide an effective and efficient method for production of amorphous form of posaconazole, the one pot process using the novel crystalline forms of B-1, B-2 & B-3 benzyl posaconazole is proposed.

Processes for preparation of amorphous forms of posaconazole have been reported earlier in the art. The International patent publication WO2013042138 (A2) discloses a few one pot processes for the preparation of amorphous form of posaconazole using 5% Pd—C and 5N HCl in methanol as solvent. The WO2015059716 (A3) discloses a few processes for the preparation of amorphous form of posaconazole involving dissolving posaconazole in dichloromethane, stirring the reaction mixture, filtering the reaction mixture, adding the filtrate to methyl tertiary butyl ether (MTBE), stirring the reaction mixture, filtering the solid and then drying to get amorphous form of posaconazole. CN104370894 discloses processes for preparation of amorphous posaconazole, posaconazole dissolved in a mixed solvent of alcohols and esters, and then added drop wise to an alkane or aromatic hydrocarbon, to get amorphous posaconazole.

Patent Reference 3: PCT Publication WO2015059716 (A3);
Patent Reference 4: Chinese patent application CN104370894;

The above reported disclosures for the preparation of amorphous form of posaconazole suffers various disadvantages with respect to the yield and quality of the amorphous posaconazole. In some cases of one pot processes the use of heavy metal catalysts for the debenzylation followed by isolation of amorphous material results in rendering the higher production costs and in other disclosures involve the isolation of posaconazole solid forms followed by another step for the amorphization which again result in the increase in the production costs and time.

Nevertheless, the present invention aims to provide a process for the preparation of amorphous posaconazole which is easy to operate, suitable for industrial scale production, cost effective and high yielding.

The present disclosure also aims to provide a one pot process for the preparation of amorphous posaconazole using novel crystalline polymorphic form B-3 of benzyl posaconazole.

BRIEF DESCRIPTION OF THE ACCOMPANYING FIGURES

In order that the disclosure may be readily understood and put into practical effect, reference will now be made to exemplary embodiments as illustrated with reference to the accompanying figures. The figures together with a detailed description below, are incorporated in and form part of the specification, and serve to further illustrate the embodiments and explain various principles and advantages, in accordance with the present disclosure wherein.

Figure 1:
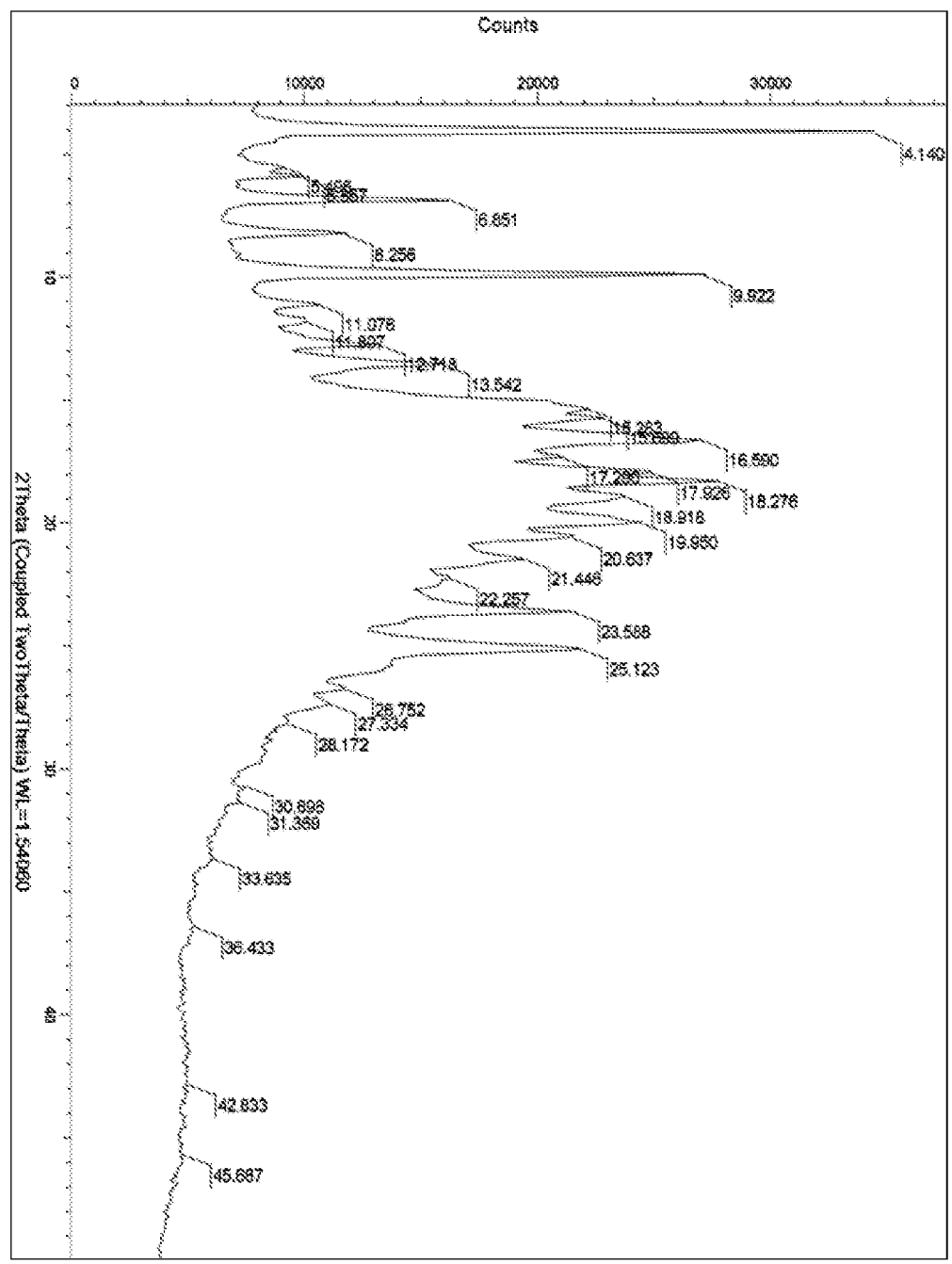
FIG. 1 shows the XRD of crystalline form B-1 of 4-(4-(4-(4-(((3R,5R)-5-((1H-1,2,4-triazol-1-yl)methyl)-5-(2,4-difluorophenyl)tetrahydrofuran-3-yl)methoxy)phenyl)piperazin-1-yl)phenyl)-1-((2S,3S)-2-(benzyloxy)pentan-3-yl)-1H-1,2,4-triazol-5(4H)-one of the structural formula (III)

The method of analysis of the compounds represented in the figures as above are as below:
PXRD Analysis About 300 mg of powder sample was taken onto the sample holder and was tightly packed on the sample holder uniformly by means of glass slide and Powder X-ray diffraction was recorded on Bruker D8 Advance diffractometer (Bruker-AXS, Karlsruhe, Germany) using Cu-Kα X-radiation (λ=1.5406 Å) at 40 kV and 30 mA powder. X-ray diffraction patterns were collected over the 2θ range 3-50° at a scan rate of 1°/min.
DSC Analysis DSC was performed on a Mettler Toledo DSC 822e module. 4-6 mg of sample was placed in crimped but vented aluminium sample pans. The temperature range was from 30-250° C. @ 10° C./min. Samples were purged by a stream of nitrogen flowing at 80 mL/min.
IR Analysis IR was performed on a Fisher Scientific (NICOLET-iS50-FTIR). About 5 mg of sample was spread over the region of diamond ATR sampling station and collected the sample spectrum between 4000 cm-1 to 400 cm-1 to obtain a spectrum of suitable intensity (above 60% transmission at 2000 cm-1).

DETAILED DESCRIPTION OF THE DISCLOSURE

The present invention relates to crystalline forms of benzyl posaconazole of structural formula III useful in the preparation of posaconazole represented by the following structural formula-IV.

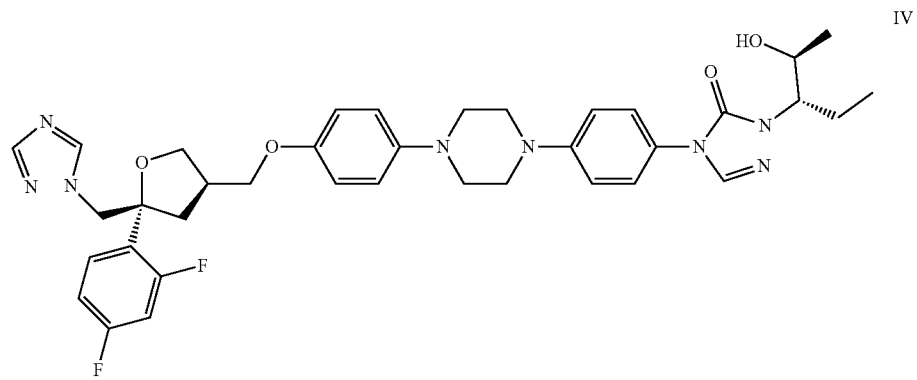 [SMILES: CC[C@H](NC(=O)N(C=N)c1ccc(N2CCN(c3ccc(OC[C@@H]4CO[C@@](CN/C=N\C=N)(c5ccc(F)cc5F)C4)cc3)CC2)cc1)[C@H](C)O]

The present disclosure provides that by the condensation of ((3S,5R)-5-((1H-1,2,4-triazol-1-yl)methyl)-5-(2,4-difluorophenyl)tetrahydrofuran-3-yl) methyl 4-methylbenzenesulfonate represented by the following structural formula (I)

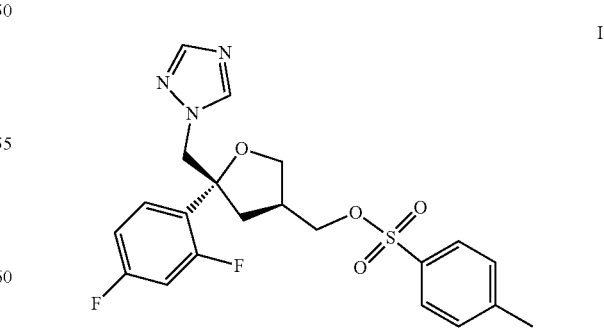

and 1-((2S,3S)-2-(benzyloxy)pentan-3-yl)-4-(4-(4-(4-hydroxyphenyl)piperazin-1-yl)phenyl)-1H-1,2,4-triazol-5(4H)-one represented by the following structural formula (II)

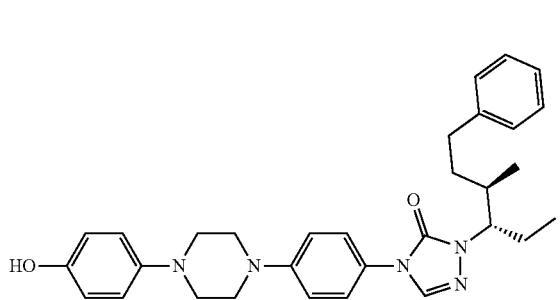

to yield 4-(4-(4-(4-(((3R,5R)-5-((1H-1,2,4-triazol-1-yl)methyl)-5-(2,4-difluorophenyl)tetrahydrofuran-3-yl)methoxy)phenyl)piperazin-1-yl)phenyl)-1-((2S,3S)-2-(benzyloxy)pentan-3-yl)-1H-1,2,4-triazol-5(4H)-one represented by the following structural formula (III) and thereby novel crystalline polymorphs B-1, B-2 & B-3 of benzyl posaconazole of structural formula (III).

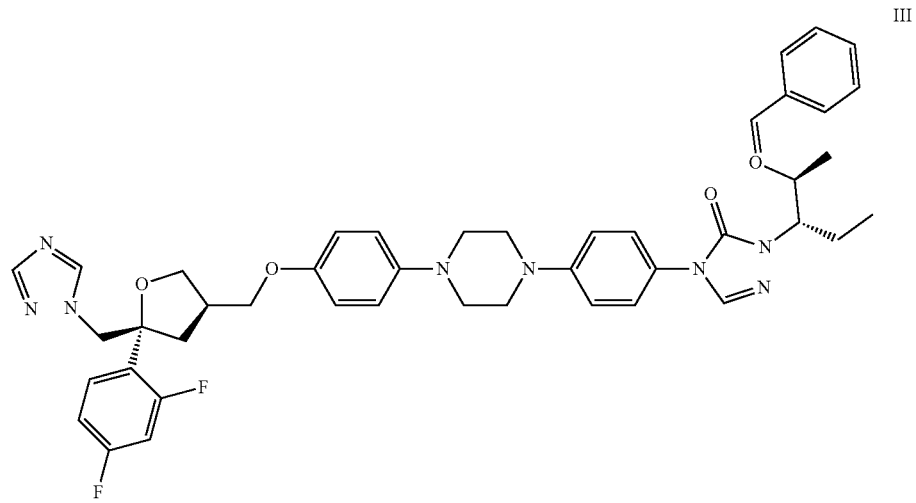

The first aspect of the present invention is to provide for stable crystalline form B-1 of the benzyl posaconazole of structural formula-III. The crystalline form B-1 possess prominent 2θ values as 4.14, 6.85, 9.92, 15.28, 15.69, 16.59, 17.29, 17.92, 18.27, 18.91, 20.63, 19.95, 23.58, and 25.12±0.2 degrees of 2θ.

The present invention provides a process for preparing the crystalline form B-1 as follows:

To a solution of 1-((2S,3S)tac-2-(benzyloxy)pentan-3-yl)-4-(4-(4-(4-hydroxyphenyl)piperazin-1-yl)phenyl)-1H-1,2,4-triazol-5(4H)-one of the structural formula (II) in a polar organic solvent is treated with an alkali solution in a lower temperature of about 5-10° C. and stirred for 10 minutes followed by addition of ((3S,5R)-5-((1H-1,2,4-triazol-1-yl)methyl)-5-(2,4-difluorophenyl)tetrahydrofuran-3-yl)methyl 4-methyl benzenesulfonate of the structural formula (I) and reaction mass was slowly warmed to room temperature and stirred for 40-45 h. The reaction mass was diluted with an aliphatic ester solvent and cooled to 10-20° C. followed by addition of water and stirred.

Layers were separated; organic layer was collected. Aqueous layer was again extracted with an aliphatic ester solvent. Combined organic layers were washed with water and concentrated. To the above residue was added a halogenated hydrocarbon solvent and an aliphatic hydrocarbon solvent and stirred at 28±5° C. for 2 h and then cooled to 0-10° C. and stirred for 1 h. Solid was filtered; washed with aliphatic hydrocarbon solvent. Dried under VTD at 50° C. to yield 4-(4-(4-(4-(((3R,5R)-5-((1H-1,2,4-triazol-1-yl)methyl)-5-(2,4-difluorophenyl)tetrahydrofuran-3-yl)methoxy)phenyl)piperazin-1-yl)phenyl)-1-((2S,3S)-2-(benzyloxy)pentan-3-yl)-1H-1,2,4-triazol-5(4H)-one of the structural formula (III) of crystalline Form B-1.

The second aspect of the present invention is to provide for stable crystalline form B-2 of the benzyl posaconazole of structural formula-III. The crystalline form B-2 possess prominent 2θ values as 4.20, 9.27, 14.22, 15.46, 15.82, 16.45, 17.31, 19.09, 20.47, 21.18, and 24.74±0.2 degrees of 2θ. The present invention provides a process for preparing the crystalline form B-2 as follows:

To a solution of 1-((2S,3S)-2-(benzyloxy)pentan-3-yl)-4-(4-(4-(4-hydroxyphenyl)piperazin-1-yl)phenyl)-1H-1,2,4-triazol-5(4H)-one of the structural formula (II) was dissolved in a polar organic solvent at 25±5° C. at 5-10° C. an alkali solution was added to the reaction mixture and was stirred for 10-30 minutes. ((3S,5R)-5-((1H-1,2,4-triazol-1-yl)methyl)-5-(2,4-difluorophenyl)tetrahydrofuran-3-yl) methyl 4-methylbenzenesulfonate was added to the reaction mixture and continued to stir for 1 h at 5-10° C. Reaction temperature was raised to 28±2° C. and stirred for 40-45 h. An aliphatic ester solvent (5.0 vol.) was added to the reaction mass and cooled to 15-20° C. followed by addition of water (5.0 vol.) and stirred. Layers were separated; organic layer was collected. Aqueous layer was again extracted with an aliphatic ester solvent Combined organic layers were washed with water (3 vol.) and concentrated partially. To the partially concentrated solution was added aliphatic hydrocarbon solvent and stirred at 40±5° C. for 30 min and then slowly cooled to 25±2° C. and continue to stir at 25±2° C. for 2 h. The above mixture was cooled to 0-5° C. and stirred for 1 h. Solid was filtered; washed with aliphatic hydrocarbon solvent. Dried under VTD at 50° C. to yield 4-(4-(4-(4-(((3R,5R)-5-((1H-1,2,4-triazol-1-yl)methyl)-5-(2,4-difluorophenyl)tetrahydrofuran-3-yl)methoxy)phenyl)piperazin-1-yl)phenyl)-1-((2S,3S)-2-(benzyloxy)pentan-3-yl)-1H-1,2,4-triazol-5(4H)-one of the structural formula (III) of crystalline Form B-2.

The third aspect of the present invention is to provide for stable crystalline form B-3 of the benzyl posaconazole of structural formula-III. The crystalline form B-3 possess prominent 2θ values as 7.07, 14.49, 15.68, 16.50, 18.05, 20.13, 20.87, 22.85, and 24.42±0.2 degrees of 2θ.

The present invention provides a process for preparing the crystalline form B-3 as follows:

To a solution of 1-((2S,3S)-2-(benzyloxy)pentan-3-yl)-4-(4-(4-(4-hydroxyphenyl)piperazin-1-yl)phenyl)-1H-1,2,4-triazol-5(4H)-one of the structural formula (II) was dissolved in a polar organic solvent at 25±2° C. under nitrogen atmosphere and cooled to 10-20° C. An alkali solution was added to the reaction mixture and was stirred for 10 minutes. ((3S,5R)-5-((1H-1,2,4-triazol-1-yl)methyl)-5-(2,4-difluorophenyl)tetrahydrofuran-3-yl)methyl 4-methylbenzenesulfonate was added to the reaction mixture and continued to stir for 1 h at 10-20° C. Reaction temperature was raised to 28±2° C. and stirred for 45-50 h. An aliphatic ester solvent was added to the reaction mass and cooled to 15-20° C. followed by addition of water, reaction mass was slowly warmed to 25±2° C. and stirred. Layers were separated; organic layer was collected. Aqueous layer was again extracted with aliphatic ester solvent. Combined organic layers were washed with water (3 vol.) and organic layer was concentrated partially. Cooled the above partially concentrated solution to 25±2° C. and was added an aliphatic hydrocarbon solvent stirred at 28±2° C. for 30 min and further diluted with aliphatic hydrocarbon solvent heated to 42±2° C., stirred for 30 min and then slowly cooled to 28±2° C. and continue to stir at 28±2° C. for 2 h. The above mixture was cooled to 0-5° C. and stirred for 1 h. Solid was filtered; washed with aliphatic hydrocarbon solvent. Dried under VTD at 60±5° C. to yield 4-(4-(4-(4-(((3R,5R)-5-((1H-1,2,4-triazol-1-yl)methyl)-5-(2,4-difluorophenyl)tetrahydrofuran-3-yl)methoxy)phenyl)piperazin-1-yl)phenyl)-1-((2S,3S)-2-(benzyloxy)pentan-3-yl)-1H-1,2,4-triazol-5(4H)-one of the structural formula (III) of crystalline Form B-3.

The fourth aspect of the present invention provides for a one pot process for the preparation of amorphous posaconazole of structural formula-IV from the novel crystalline form B-3 of posaconazole intermediate i.e benzyl posaconazole of structural formula-III The present disclosure also provides for the debenzylation of the benzyl posaconazole with concentrated hydrochloric acid at elevated temperature followed by addition of an organic solvent, neutralisation by washing with a base, partial concentration and addition of an organic solvent which is followed by addition to a hydrocarbon solvent at lower temperature and slowly bringing it to ambient temperature and filtration followed by washing with hydrocarbon solvent and drying to result in amorphous form of posaconazole of structural formula (IV).

4-(4-(4-(4-(((3R,5R)-5-((1H-1,2,4-triazol-1-yl)methyl)-5-(2,4-difluorophenyl)tetrahydrofuran-3-yl)methoxy)phenyl)piperazin-1-yl)phenyl)-1-((2S,3S)-2-(benzyloxy)pentan-3-yl)-1H-1,2,4-triazol-5(4H)-one of the structural formula (III) of crystalline form B-3 was charged to Concentrated Hydrochloric Acid at 25±2° C. The reaction mixture was slowly heated to 63±2° C. and stirred at 63±2° C. for 2 to 3 h. Reaction mass was cooled to 25±2° C. and a halogenated hydrocarbon solvent was charged, stirred and layers were separated. The aqueous layer was added halogenated hydrocarbon solvent and water. The contents were cooled to 15±5° C., pH of the above mass was adjusted to 10 to 12 pH using alkaline solution. Layers were separated. The aqueous layer was re-extracted with halogenated hydrocarbon solvent. Combined organic layers were washed with 10% aqueous sodium hydroxide, followed by water. Organic layer was concentrated under vacuum at 43±2° C. up to 4.0 volume stage. An aliphatic ketone solvent was added to the reaction mass. This reaction mass was added dropwise to a hydrocarbon solvent at a lower temperature with constant stirring, the reaction mass was slowly warmed to ambient temperature and continued to stir at the same temperature for 1 hour. Filtered and washed with hydrocarbon solvent and suck dried; dried in VTD under vacuum to yield 4-[4-[4-[4-[[[(3R,5R)-5-(2,4-difluorophenyl)tetrahydro-5(1H-1,2,4-triazol-1-ylmethyl)-3-furanyl]methoxy]phenyl]-1-piperazinyl]phenyl]-2-[(1S,2S)-1-ethyl-2-hydroxy propyl]-2,4-dihydro-3H-1,2,4-triazol-3-one of the structural formula (IV) of amorphous form.

The fifth aspect of the present invention provides for a process for the preparation of crystalline Form-I of posaconazole of structural formula-IV from amorphous form of posaconazole.

The amorphous form of posaconazole of the structural formula (IV) was dissolved in a halogenated organic solvent to obtain a clear solution. The above solution was evaporated to obtain a solidified material. The solid product was dried to obtain 4-[4-[4-[4-[[[(3R,5R)-5-(2,4-difluorophenyl)tetrahydro-5(1H-1,2,4-triazol-1-ylmethyl)-3-furanyl]

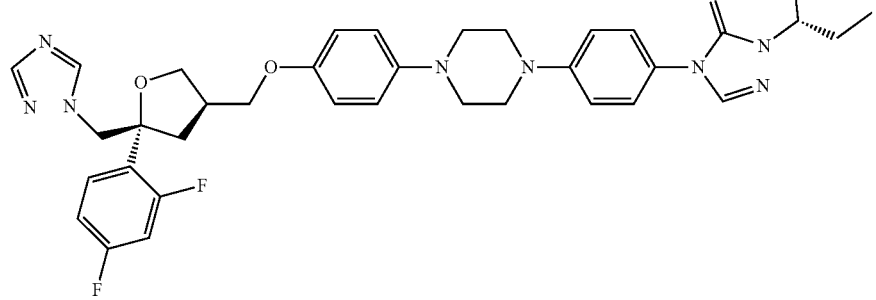

methoxy]phenyl]-1-piperazinyl]phenyl]-2-[(1S,2S)-1-ethyl-2-hydroxy propyl]-2,4-dihydro-3H-1,2,4-triazol-3-one of the structural formula (IV) in crystalline form I.

As discussed in the above aspects of invention the term "polar organic solvent" refers to Dimethyl sulfoxide, dimethyl formamide and the like; "an aliphatic ester solvent" refers to ethyl acetate, methyl acetate, isopropyl acetate and the like; "a halogenated hydrocarbon solvent" refers to dichloromethane, chloroform, dichloroethane, carbon tetrachloride and the like; "alkali solution" refers to the aqueous solution of sodium hydroxide, potassium hydroxide, sodium bicarbonate and the like; "aliphatic hydrocarbon solvent" refers to hexane, heptane, cylcohexane, pentane and the like. The term lower temperature refers to a temperature between 0-25° C.

Effect of the Invention 4-(4-(4-(4-(((3R,5R)-5-((1H-1,2,4-triazol-1-yl)methyl)-5-(2,4-difluorophenyl)tetrahydrofuran-3-yl)methoxy)phenyl)piperazin-1-yl)phenyl)-1-((2S,3S)-2-(benzyloxy) pentan-3-yl)-1H-1,2,4-triazol-5(4H)-one of the structural formula (III) generated as an intermediate in the method for production of the present invention crystallizes well, is easy to separate from the by-products and easy to handle. Therefore, the crystalline polymorphs B-1, B-2 & B-3 of the present invention serves as excellent intermediates for the industrial production of posaconazole.

4-[4-[4-[4-[[(3R,5R)-5-(2,4-difluorophenyl)tetrahydro-5 (1H-1,2,4-triazol-1-ylmethyl)-3-furanyl]methoxy]phenyl]-1-piperazinyl]phenyl]-2-[(1S,2S)-1-ethyl-2hydroxypropyl]-2,4-dihydro-3H-1,2,4-triazol-3-one of the structural formula (IV) amorphous form prepared from the instant invention is stable and the production cycle is short with high yield recovery suitable for industrial production and use of common solvents and inexpensive reagents.

EXAMPLES

Scheme:

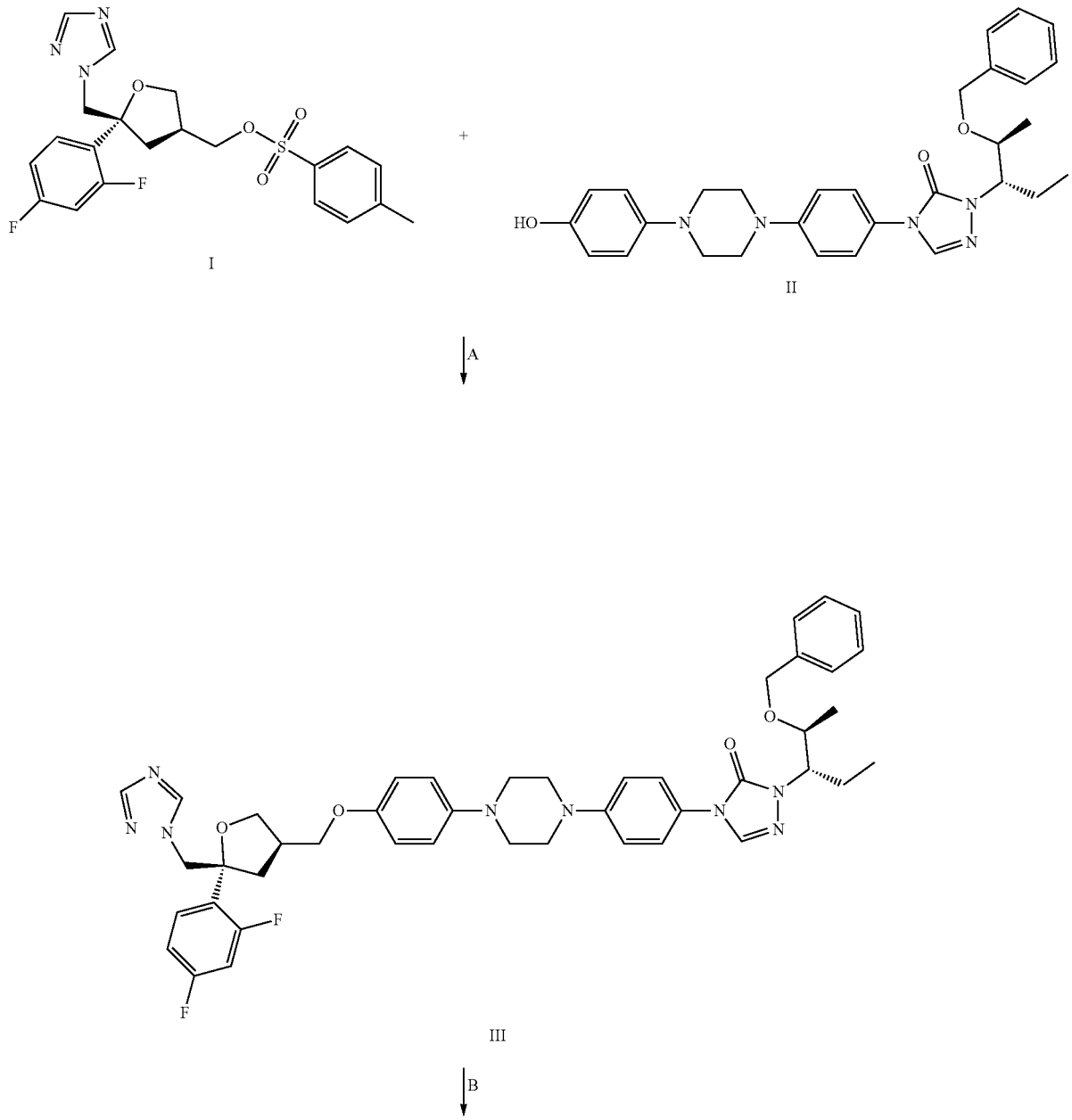

-continued

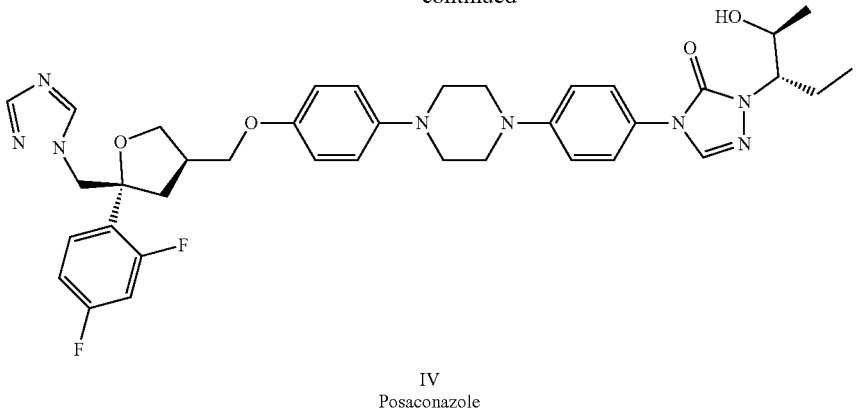

IV
Posaconazole

Reagents:
A) Sodium hydroxide/water/Dimethyl sulfoxide;
B) Concentrated Hydrochloric Acid/Dichloromethane/Aqueous Sodium Hydroxide solution/Acetone/Cyclohexane;

The scheme is represented by following examples. These examples are for illustration only and hence should not be construed as limitation of the scope of invention.

Example 1: Preparation of 4-(4-(4-(4-(((3R,5R)-5-((1H-1,2,4-triazol-1-yl)methyl)-5-(2,4-difluorophenyl)tetrahydrofuran-3-yl)methoxy)phenyl)piperazin-1-yl)phenyl)-1-((2S,3S)-2-(benzyloxy)pentan-3-yl)-1H-1,2,4-triazol-5(4H)-one of the Structural Formula (III) of Crystalline Form B-1

1-((2S,3S)-2-(benzyloxy)pentan-3-yl)-4-(4-(4-(4-hydroxyphenyl)piperazin-1-yl)phenyl)-1H-1,2,4-triazol-5(4H)-one (25.0 g) of the structural formula (II) was dissolved in Dimethyl sulfoxide (6.0 vol.) at 25±2° C. and cooled to 5-10° C. 25% aqueous sodium hydroxide solution (1.3 eq.) was added to the reaction mixture and was stirred for 10 minutes. ((3S,5R)-5-((1H-1,2,4-triazol-1-yl)methyl)-5-(2,4-difluorophenyl)tetrahydrofuran-3-yl)methyl 4-methylbenzenesulfonate of the structural formula (I) (25.16 g) was added to the reaction mixture and continued to stir for 2 h at 5-10° C. Reaction temperature was raised to 28±2° C. and stirred for 40-45 h. Ethyl acetate (5.0 vol.) was added to the reaction mass and cooled to 15-20° C. followed by addition of water (5.0 vol.) and stirred. Layers were separated; Ethyl acetate layer was collected. Aqueous layer was again extracted with Ethyl acetate (3 vol.). Combined organic layers were washed with water (3 vol.) and concentrated. To the residue was added dichloromethane (2.0 vol.) and Heptane (7.0 vol.) and stirred at 28±2° C. for 2 h and then cooled to 0-5° C. and stirred for 1 h. Solid was filtered; washed with Heptane (5 vol.). Dried under VTD at 50° C. to yield 4-(4-(4-(4-(((3R,5R)-5-((1H-1,2,4-triazol-1-yl)methyl)-5-(2,4-difluorophenyl)tetrahydrofuran-3-yl)methoxy)phenyl)piperazin-1-yl)phenyl)-1-(2S,3S)-2-(benzyloxy)pentan-3-yl)-1H-1,2,4-triazol-5(4H)-one of the structural formula (III) of crystalline Form B-1 with 95%.

Example-2: Preparation of 4-(4-(4-(4-(((3R,5R)-5-((1H-1,2,4-triazol-1-yl)methyl)-5-(2,4-difluorophenyl)tetrahydrofuran-3-yl)methoxy)phenyl)piperazin-1-yl)phenyl)-1-((2S,3S)-2-(benzyloxy)pentan-3-yl)-1H-1,2,4-triazol-5(4H)-one of the Structural Formula (III) of Crystalline Form B-2

1-((2S,3S)-2-(benzyloxy)pentan-3-yl)-4-(4-(4-(4-hydroxyphenyl)piperazin-1-yl)phenyl)-1H-1,2,4-triazol-5(4H)-one (25.0 g.) of the structural formula (II) was dissolved in Dimethyl sulfoxide (6.0 vol.) at 25±2° C. and cooled to 5-10° C. 25% aqueous sodium hydroxide solution (1.3 eq.) was added to the reaction mixture and was stirred for 10 minutes. ((3S,5R)-5-((1H-1,2,4-triazol-1-yl)methyl)-5-(2,4-difluorophenyl)tetrahydrofuran-3-yl)methyl 4-methylbenzenesulfonate of the structural formula (I) (25.16 g) was added to the reaction mixture and continued to stir for 1 h at 5-10° C. Reaction temperature was raised to 28±2° C. and stirred for 40-45 h. Ethyl acetate (5.0 vol.) was added to the reaction mass and cooled to 15-20° C. followed by addition of water (5.0 vol.) and stirred. Layers were separated Ethyl acetate layer was collected. Aqueous layer was again extracted with Ethyl acetate (3 vol.). Combined organic layers were washed with water (3 vol.) and concentrated partially to contain 3.0 Vol. of Ethyl acetate. To the partially concentrated solution was added Heptane (8.0 vol.) and stirred at 40±5° C. for 30 min and then slowly cooled to 25±2° C. and continue to stir at 25±2° C. for 2 h. The above mixture was cooled to 0-5° C. and stirred for 1 h. Solid was filtered; washed with Heptane (5 vol.). Dried under VTD at 50° C. to yield 4-(4-(4-(4-(((3R,5R)-5-((1H-1,2,4-triazol-1-yl)methyl)-5-(2,4-difluorophenyl)tetrahydrofuran-3-yl)methoxy)phenyl)piperazin-1-yl)phenyl)-1-((2S,3S)-2-(benzyloxy)pentan-3-yl)-1H-1,2,4-triazol-5(4H)-one of the structural formula (III) of crystalline Form B-2 with 88% yield.

| Characteristic Physico-Chemical Data of Crystalline Form B-1 of the Compound of Structural Formula III | |
|---|---|
| Physical appearance: | Off-white to white solid |
| X-ray Powder Diffraction Pattern: | See FIG. 1 and Table 1 |

Figure 2:
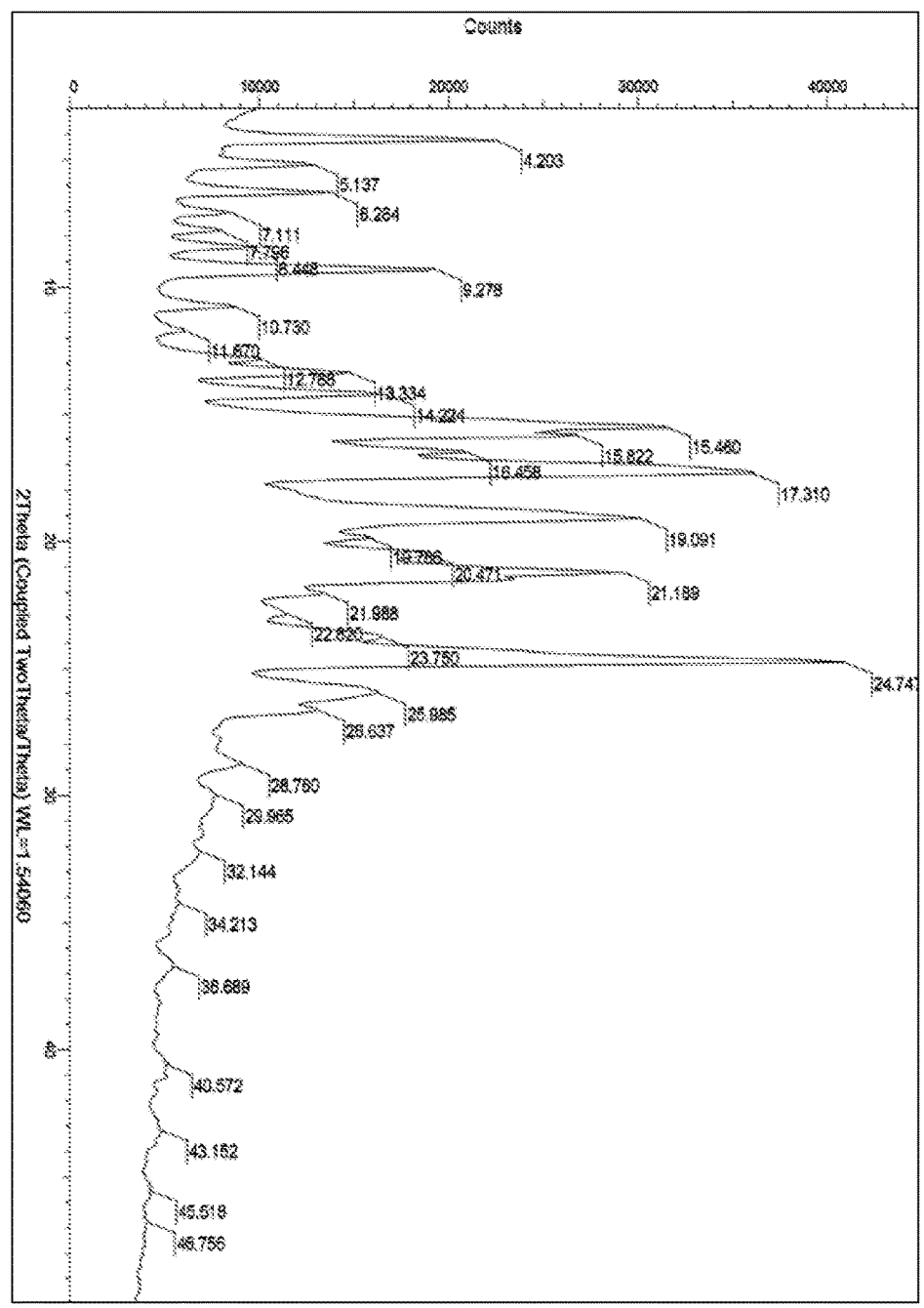
FIG. 2 shows the XRD of crystalline form B-2 of 4-(4-(4-(4-(((3R,5R)-5-((1H-1,2,4-triazol-1-yl)methyl)-5-(2,4-difluorophenyl)tetrahydrofuran-3-yl)methoxy)phenyl)piperazin-1-yl)phenyl)-1-((2S,3S)-2-(benzyloxy)pentan-3-yl)-1H-1,2,4-triazol-5(4H)-one of the structural formula (III)

| Characteristic Physico-Chemical Data of Crystalline Form B-2 of the Compound of Structural Formula III | |
|---|---|
| Physical appearance: | Off-white to white solid |
| X-ray Powder Diffraction Pattern: | See FIG. 2 and Table 2 |

Example-3: Preparation of 4-(4-(4-(4-(((3R,5R)-5-((1H-1,2,4-triazol-1-yl)methyl)-5-(2,4-difluorophenyl)tetrahydrofuran-3-yl)methoxy)phenyl)piperazin-1-yl)phenyl)-1-((2S,3S)-2-(benzyloxy)pentan-3-yl)-1H-1,2,4-triazol-5(4H)-one of the Structural Formula (III) of Crystalline Form B-3

1-((2S,3S)-2-(benzyloxy)pentan-3-yl)-4-(4-(4-(4-hydroxyphenyl)piperazin-1-yl)phenyl)-1H-1,2,4-triazol-5(4H)-one (4.0 Kg, 1.0 eq.) of the structural formula (II) was dissolved in Dimethyl sulfoxide (6.0 vol.) at 25±2° C. under nitrogen and cooled to 15-20° C. 25% aqueous sodium hydroxide solution (1.3 eq.) was added to the reaction mixture and was stirred for 10 minutes. ((3S,5R)-5-((1H-1,2,4-triazol-1-yl)methyl)-5-(2,4-difluorophenyl)tetrahydrofuran-3-yl)methyl 4-methylbenzenesulfonate of the structural formula (I) (4.02 Kg) was added to the reaction mixture and continued to stir for 1 h at 15-20° C. Reaction temperature was raised to 28±2° C. and stirred for 45-50 h. Ethyl acetate (5.0 vol.) was added to the reaction mass and cooled to 15-20° C. followed by addition of water (5.0 vol.), reaction mass was slowly warmed to 25±2° C. and stirred. Layers were separated; organic layer was collected. Aqueous layer was again extracted with Ethyl acetate (3 vol.). Combined organic layers were washed with water (3 vol.) and organic layer was concentrated partially to contain 5.0 Vol. of Ethyl acetate. Cooled the partially concentrated solution to 25±2° C. and was added n-Heptane (5.0 vol.), stirred at 28±2° C. for 30 min and further diluted with n-Heptane (2.0 vol.) heated to 42±2° C., stirred for 30 min and then slowly cooled to 28±2° C. and continue to stir at 28±2° C. for 2 h. The above mixture was cooled to 0-5° C. and stirred for 1 h. Solid was filtered; washed with Heptane (5 vol.). Dried under VTD at 60±5° C. to yield 4-(4-(4-(4-(((3R,5R)-5-((1H-1,2,4-triazol-1-yl)methyl)-5-(2,4-difluorophenyl)tetrahydrofuran-3-yl)methoxy)phenyl)piperazin-1-yl)phenyl)-1-((2S,3S)-2-(benzyloxy)pentan-3-yl)-1H-1,2,4-triazol-5(4H)-one of the structural formula (III) of crystalline Form B-3 with 96% yield.

Figure 3:
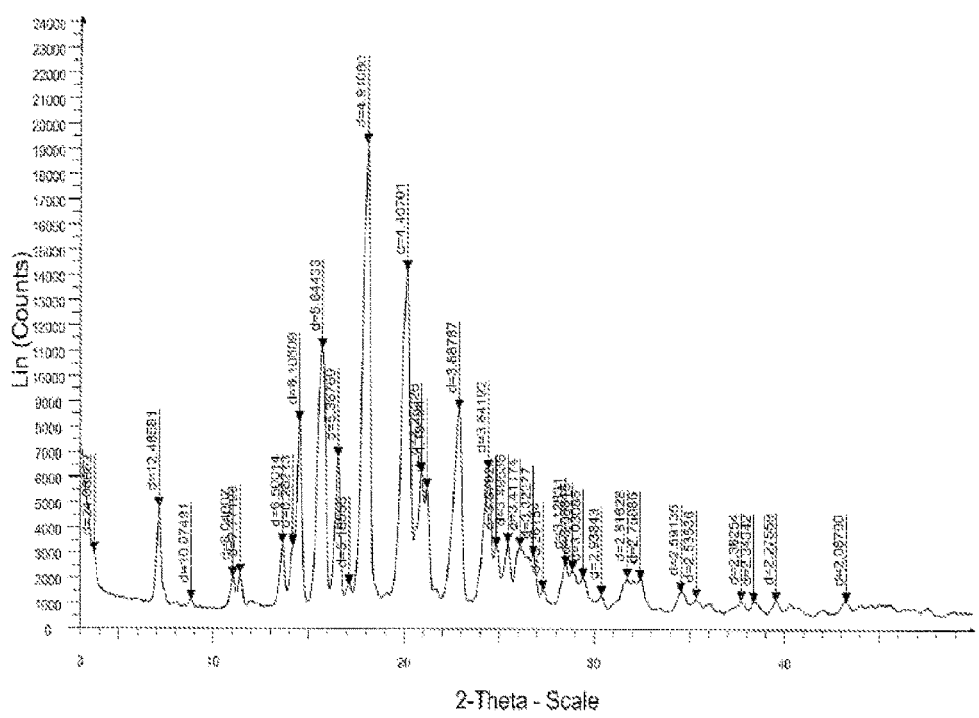
FIG. 3 shows the XRD of crystalline form B-3 of 4-(4-(4-(4-(((3R,5R)-5-((1H-1,2,4-triazol-1-yl)methyl)-5-(2,4-difluorophenyl)tetrahydrofuran-3-yl)methoxy)phenyl)piperazin-1-yl)phenyl)-1-((2S,3S)-2-(benzyloxy)pentan-3-yl)-1H-1,2,4-triazol-5(4H)-one of the structural formula (III)
Figure 4:
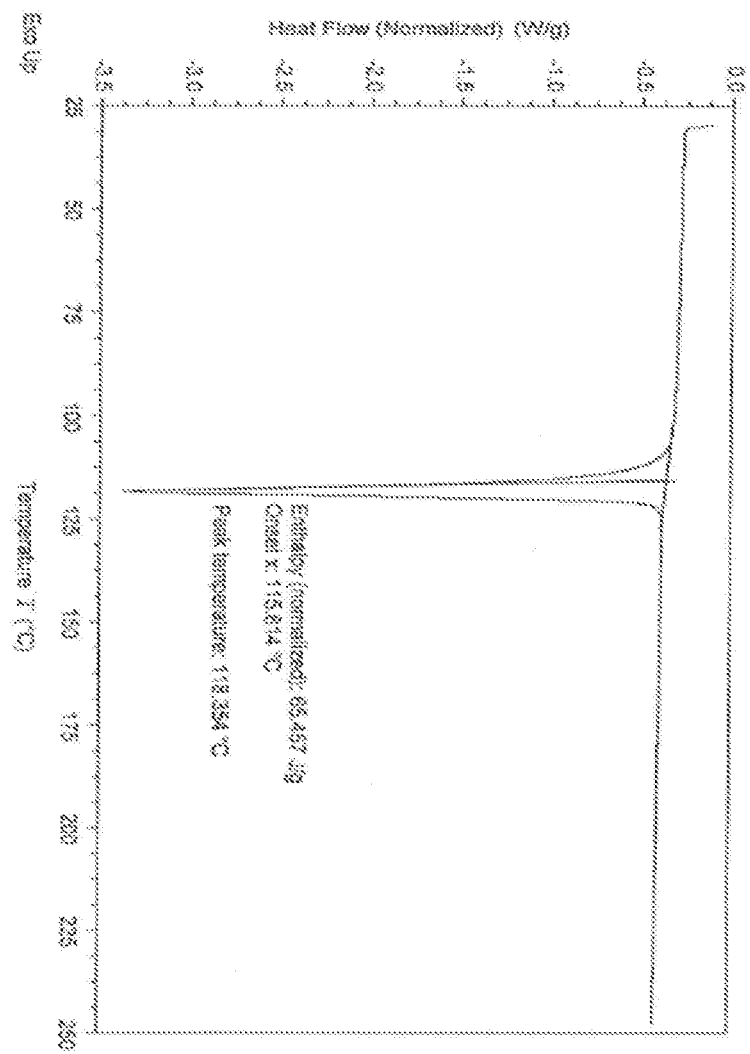
FIG. 4 shows the DSC of crystalline form B-3 of 4-(4-(4-(4-(((3R,5R)-5-((1H-1,2,4-triazol-1-yl)methyl)-5-(2,4-difluorophenyl)tetrahydrofuran-3-yl)methoxy)phenyl)piperazin-1-yl)phenyl)-1-((2S,3S)-2-(benzyloxy)pentan-3-yl)-1H-1,2,4-triazol-5(4H)-one of the structural formula (III)
Figure 5:
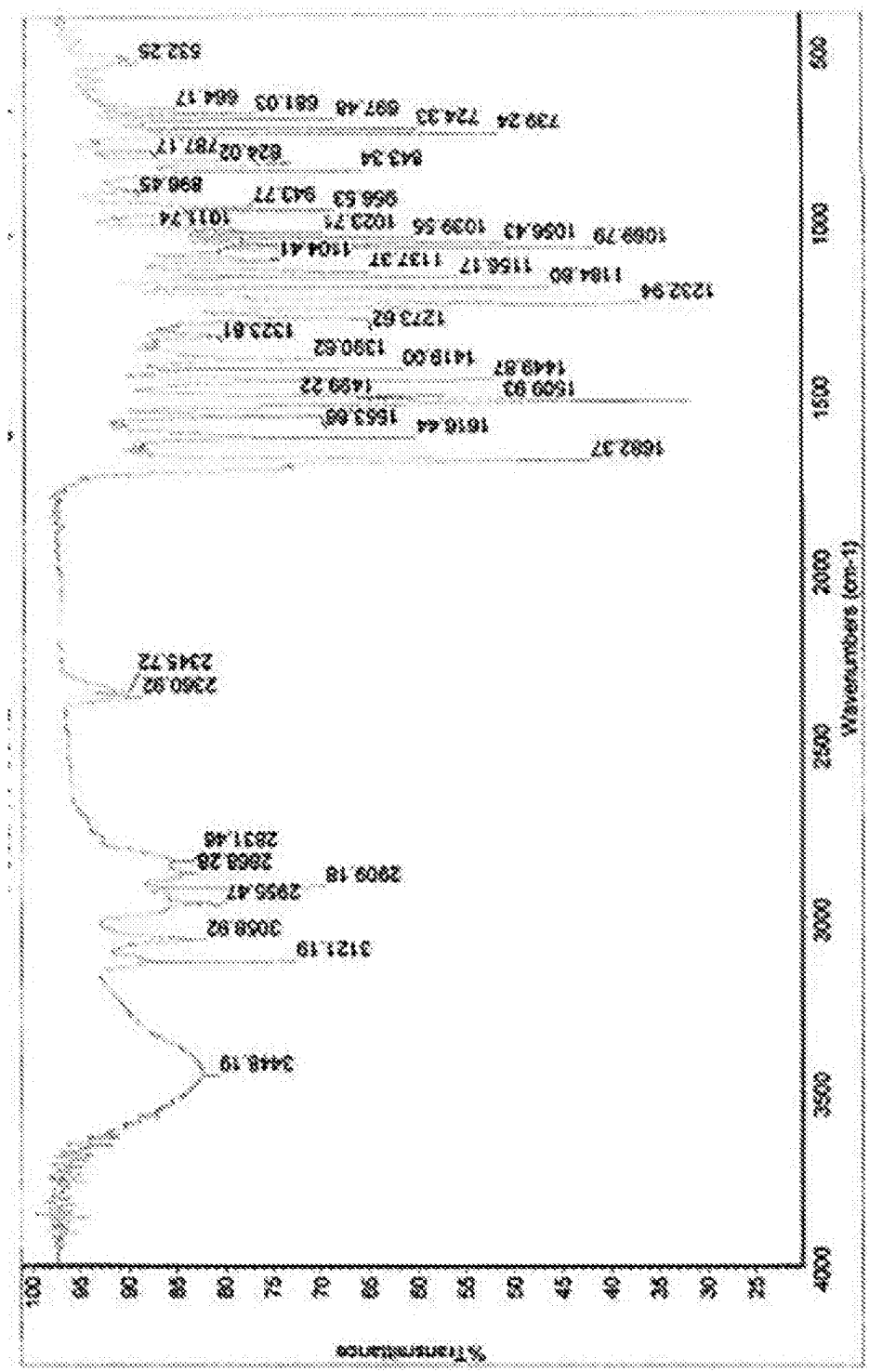
FIG. 5 shows the IR of crystalline form B-3 of 4-(4-(4-(4-(((3R,5R)-5-((1H-1,2,4-triazol-1-yl)methyl)-5-(2,4-difluorophenyl)tetrahydrofuran-3-yl)methoxy)phenyl)piperazin-1-yl)phenyl)-1-((2S,3S)-2-(benzyloxy)pentan-3-yl)-1H-1,2,4-triazol-5(4H)-one of the structural formula (III)

| Characteristic Physico-Chemical Data of Crystalline Form B-3 of the Compound of Structural Formula III | |
|---|---|
| Physical appearance: | Off-white to white solid |
| X-ray Powder Diffraction Pattern: | See FIG. 3 and Table 3 |
| DSC: | See FIG. 4 |
| IR: | See FIG. 5 |

Example 4: Preparation of 4-[4-[4-[4-[[(3R,5R)-5-(2,4-difluorophenyl)tetrahydro-5(1H-1,2,4-triazol-1-ylmethyl)-3-furanyl]methoxy]phenyl]-1-piperazinyl]phenyl]-2-[(1S,2S)-1-ethyl-2-hydroxypropyl]-2,4-dihydro-3H-1,2,4-triazol-3-one of the Structural Formula (IV) of Amorphous Form 4-(4-(4-(4-(((3R,5R)-5-((1H-1,2,4-triazol-1-yl)methyl)-5-(2,4-difluorophenyl)tetrahydrofuran-3-yl)methoxy)phenyl)piperazin-1-yl)phenyl)-1-((2S,3S)-2-(benzyloxy)pentan-3-yl)-1H-1,2,4-triazol-5(4H)-one of the structural formula (III) (10.0 g.) of crystalline form B-3 was charged to a RBF containing Concentrated Hydrochloric Acid (5.0 vol.) at 25±2° C. The reaction mixture was slowly heated to 62±2° C. and stirred at 62±2° C. for 2 to 3 h. Reaction mass was cooled to 25±2° C. and Dichloromethane (5.0 vol.×2 times) was charged, stirred for 30 minutes and layers were separated. The aqueous layer was added dichloromethane (6.0 vol.) and water (5.0 vol.). The contents were cooled to 15±5° C., pH of the above mass was adjusted to 9 to 10 pH using 25% aqueous sodium hydroxide. Layers were separated. The aqueous layer was re-extracted with Dichloromethane (5.0 vol.×2 times). Combined dichloromethane layers were washed with 10% aqueous sodium hydroxide (5.0 vol.×2 times), followed by water (5.0 vol.). Dichloromethane layer was dried over anhydrous sodium sulphate and concentrated the dichloromethane layer under vacuum at 43±2° C. up to 3.0 volume stage. This reaction mass was cooled to 25° C. and was added Acetone (4.0 vol.). Cyclohexane (20.0 vol.) was added to this reaction mass at same temperature and warmed to 45±2° C. and stirred for 30 minutes. The reaction mass was slowly cooled to 25±2° C. Filtered and washed with Cyclohexane (5.0 vol.) and suck dried; dried in VTD at 70±2° C. for 30 to 40 h under vacuum to yield 4-[4-[4-[4-[[(3R,5R)-5-(2,4-difluorophenyl)tetrahydro-5(1H-1,2,4-triazol-1-ylmethyl)-3-furanyl]methoxy]phenyl]-1-piperazinyl]phenyl]-2-[(1S,2S)-1-ethyl-2-hydroxy propyl]-2,4-dihydro-3H-1,2,4-triazol-3-one of the structural formula (IV) of amorphous form with 92% yield.

Example 5: Preparation of 4-[4-[4-[4-[[(3R,5R)-5-(2,4-difluorophenyl)tetrahydro-5(1H-1,2,4-triazol-1-ylmethyl)-3-furanyl]methoxy]phenyl]-1-piperazinyl]phenyl]-2-[(1S,2S)-1-ethyl-2-hydroxypropyl]-2,4-dihydro-3H-1,2,4-triazol-3-one of the Structural Formula (IV) of Crystalline Form I 4-(4-(4-(4-(((3R,5R)-5-((1H-1,2,4-triazol-1-yl)methyl)-5-(2,4-difluorophenyl)tetrahydrofuran-3-yl)methoxy)phenyl)piperazin-1-yl)phenyl)-1-((2S,3S)-2-(benzyloxy)pentan-3-yl)-1H-1,2,4-triazol-5(4H)-one of the structural formula (III) (10.0 g.) of crystalline form B-3 was charged to a RBF containing Concentrated Hydrochloric Acid (5.0 vol.) at 25±2° C. The reaction mixture was slowly heated to 62±2° C. and stirred at 62±2° C. for 2 to 3 h. Reaction mass was cooled to 25±2° C. and Dichloromethane (5.0 vol.×2 times) was charged, stirred for 30 minutes and layers were separated. The aqueous layer was added dichloromethane (6.0 vol.) and water (5.0 vol.). The contents were cooled to 15±5° C., pH of the above mass was adjusted to 9 to 10 pH using 25% aqueous sodium hydroxide. Layers were separated. The aqueous layer was re-extracted with dichloromethane (5.0 vol.×2 times). Combined dichloromethane layers were washed with 10% aqueous sodium hydroxide (5.0 vol.×2 times), followed by water (5.0 vol.). Dichloromethane layer was dried over anhydrous sodium sulphate and concentrated the dichloromethane layer under vacuum at 43±2° C. up to 3.0 volume stage. This dichloromethane solution was cooled to 25° C. and was added Acetone (4.0 vol.). This reaction mass was added dropwise to Cyclohexane (20.0 vol.) at 0 to 10° C. with constant stirring and after addition the reaction mass was slowly warmed to 25° C. and continued to stir at the same temperature for 1 hour. Filtered and washed with Cyclohexane (5.0 vol.) and suck dried; dried in VTD at 70±2° C. for 30 to 40 h under vacuum to yield 4-[4-[4-[4-[[(3R,5R)-5-(2,4-difluorophenyl)tetrahydro-5(1H-1,2,4-triazol-1-ylmethyl)-3-furanyl]methoxy]phenyl]-1-piperazinyl]phenyl]-2-[(1S,2S)-1-ethyl-2-hydroxy propyl]-2,4-dihydro-3H-1,2,4-triazol-3-one of the structural formula (IV) of amorphous form.

The above obtained amorphous form was dissolved in dichloromethane to obtain a clear solution. The above solution was evaporated at 70° C. to obtain a solidified material. The solid product was dried at 70° C. for 7 hours to obtain 4-[4-[4-[4-[[(3R,5R)-5-(2,4-difluorophenyl)tetrahydro-5

(1H-1,2,4-triazol-1-ylmethyl)-3-furanyl]methoxy]phenyl]-1-piperazinyl]phenyl]-2-[(1S,2S)-1-ethyl-2-hydroxy propyl]-2,4-dihydro-3H-1,2,4-triazol-3-one of the structural formula (IV) in crystalline form I.

Example-6: Preparation of 4-[4-[4-[4-[[(3R,5R)-5-(2,4-difluorophenyl)tetrahydro-5(1H-1,2,4-triazol-1-ylmethyl)-3-furanyl]methoxy]phenyl]-1-piperazinyl]phenyl]-2-[(1S,2S)-1-ethyl-2-hydroxypropyl]-2,4-dihydro-3H-1,2,4-triazol-3-one of the Structural Formula (IV) of Amorphous Form 4-(4-(4-(4-(((3R,5R)-5-((1H-1,2,4-triazol-1-yl)methyl)-5-(2,4-difluorophenyl)tetrahydrofuran-3-yl)methoxy)phenyl)piperazin-1-yl)phenyl)-1-((2S,3S)-2-(benzyloxy)pentan-3-yl)-1H-1,2,4-triazol-5(4H)-one of the structural formula (III) (10.0 g) of crystalline form B-3 was charged to a RBF containing Concentrated Hydrochloric Acid (5.0 vol.) at 25±2° C. The reaction mixture was slowly heated to 62±2° C. and stirred at 62±2° C. for 2 to 3 h. Reaction mass was cooled to 25±2° C. and Dichloromethane (5.0 vol.×2 times) was charged, stirred for 30 minutes and layers were separated. The aqueous layer was added dichloromethane (6.0 vol.) and water (5.0 vol.). The contents were cooled to 15±5° C., pH of the above mass was adjusted to 9 to 10 pH using 25% aqueous sodium hydroxide. Layers were separated. The aqueous layer was re-extracted with dichloromethane (5.0 vol.×2 times). Combined dichloromethane layers were washed with 10% aqueous sodium hydroxide (5.0 vol.×2 times), followed by water (5.0 vol.). Dichloromethane layer was dried over anhydrous sodium sulphate and concentrated the dichloromethane layer under vacuum at 43±2° C. up to 3.0 volume stage. Acetone (4.0 vol.) was added to mass and frozen the reaction mass by the addition of liquid Nitrogen (−95±5° C.). Cyclohexane (20.0 vol.) was added to the above reaction mass and stirred at 2±2° C. for 1 hour. Filtered and washed with Cyclohexane (5.0 vol.) and suck dried; dried in VTD at 70±2° C. for 30 to 40 h under vacuum to yield 4-[4-[4-[4-[[(3R,5R)-5-(2,4-difluorophenyl)tetrahydro-5(1H-1,2,4-triazol-1-ylmethyl)-3-furanyl]methoxy]phenyl]-1-piperazinyl]phenyl]-2-[(1S,2S)-1-ethyl-2-hydroxy propyl]-2,4-dihydro-3H-1,2,4-triazol-3-one of the structural formula (IV) of amorphous form with 75% yield.

Example-7: Preparation of 4-[4-[4-[4-[[(3R,5R)-5-(2,4-difluorophenyl)tetrahydro-5(1H-1,2,4-triazol-1-ylmethyl)-3-furanyl]methoxy]phenyl]-1-piperazinyl]phenyl]-2-[(1S,2S)-1-ethyl-2-hydroxypropyl]-2,4-dihydro-3H-1,2,4-triazol-3-one of the Structural Formula (IV) of Amorphous Form 4-(4-(4-(4-(((3R,5R)-5-((1H-1,2,4-triazol-1-yl)methyl)-5-(2,4-difluorophenyl)tetrahydrofuran-3-yl)methoxy)phenyl)piperazin-1-yl)phenyl)-1-((2S,3S)-2-(benzyloxy)pentan-3-yl)-1H-1,2,4-triazol-5(4H)-one of the structural formula (III) (350.0 g) of crystalline form B-3 was charged to a RBF containing Concentrated Hydrochloric Acid (5.0 vol.) at 25±2° C. The reaction mixture was slowly heated to 63±2° C. and stirred at 63±2° C. for 2 to 3 h. Reaction mass was cooled to 25±2° C. and Dichloromethane (5.0 vol.×2 times) was charged, stirred and layers were separated. The aqueous layer was added dichloromethane (6.0 vol.) and water (5.0 vol.). The contents were cooled to 15±5° C., pH of the above mass was adjusted to 10 to 12 pH using 25% aqueous sodium hydroxide. Layers were separated. The aqueous layer was re-extracted with dichloromethane (5.0 vol.×2 times). Combined dichloromethane layers were washed with 10% aqueous sodium hydroxide (3.0 vol.×2 times), followed by water (3.0 vol.). Dichloromethane layer was concentrated under vacuum at 43±2° C. up to 4.0 volume stage. Acetone (4.0 vol.) was added to the reaction mass. This reaction mass was added dropwise to Cyclohexane (20.0 vol.) at 10 to 14° C. with constant stirring, the reaction mass was slowly warmed to 25° C. and continued to stir at the same temperature for 1 hour. Filtered and washed with Cyclohexane (5.0 vol.) and suck dried; dried in VTD at 60±5° C. for 30 to 40 h under vacuum to yield 4-[4-[4-[4-[[(3R,5R)-5-(2,4-difluorophenyl)tetrahydro-5(1H-1,2,4-triazol-1-ylmethyl)-3-furanyl]methoxy]phenyl]-1-piperazinyl]phenyl]-2-[(1S,2S)-1-ethyl-2-hydroxy propyl]-2,4-dihydro-3H-1,2,4-triazol-3-one of the structural formula (IV) of amorphous form with 95% yield.

Figure 6:
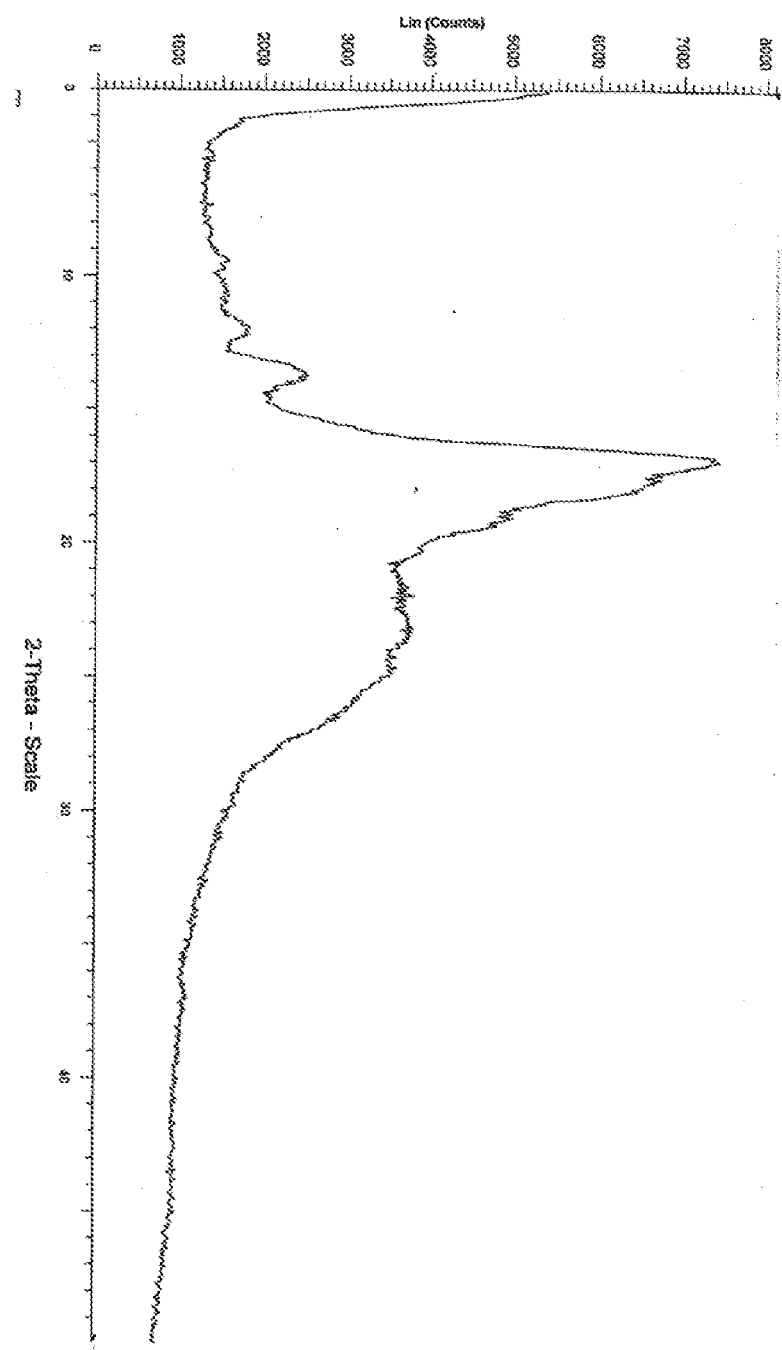
FIG. 6 shows the XRD of amorphous form of 4-[4-[4-[4-[[(3R,5R)-5-(2,4-difluorophenyl)tetrahydro-5(1H-1,2,4-triazol-1-ylmethyl)-3-furanyl]methoxy]phenyl]-1-piperazinyl]phenyl]-2-[(1S,2S)-1-ethyl-2 hydroxypropyl]-2,4-dihydro-3H-1,2,4-triazol-3-one of the structural formula (IV)
Figure 7:
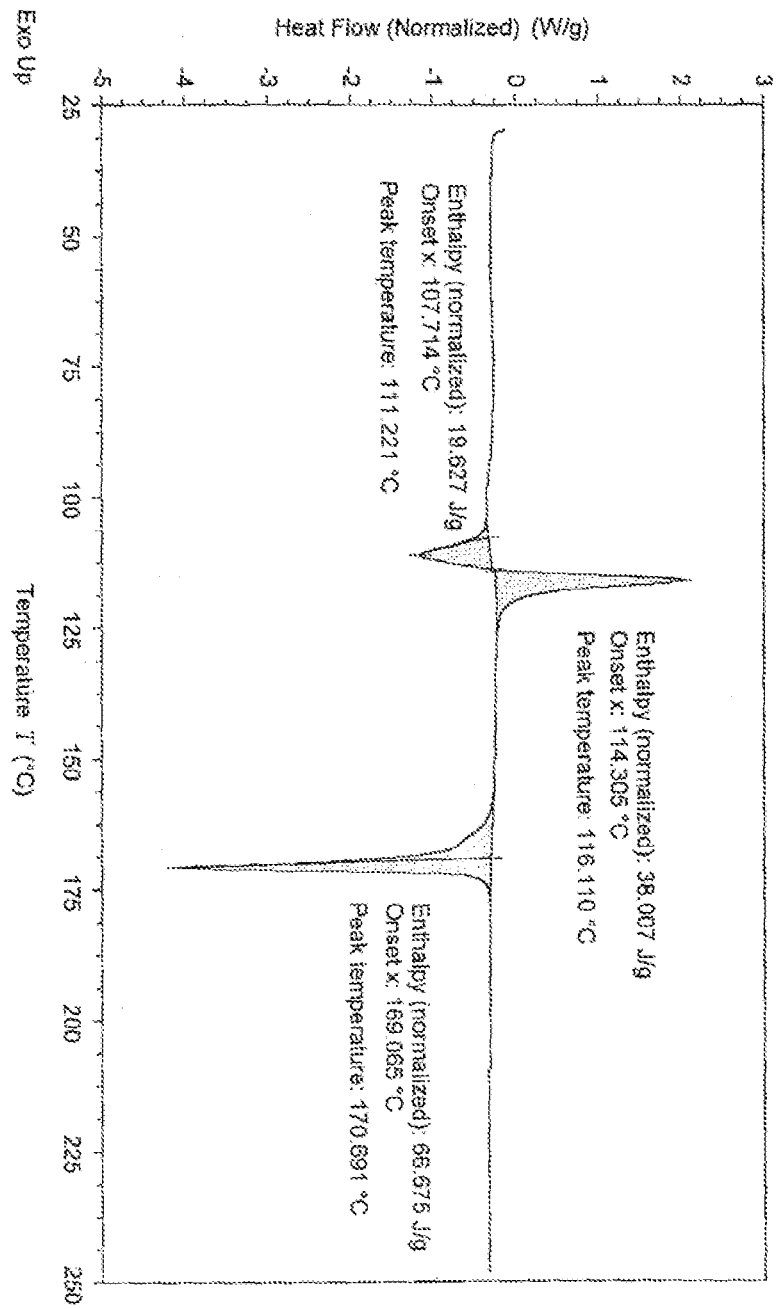
FIG. 7 shows the DSC of amorphous form of 4-[4-[4-[4-[[(3R,5R)-5-(2,4-difluorophenyl)tetrahydro-5(1H-1,2,4-triazol-1-ylmethyl)-3-furanyl]methoxy]phenyl]-1-piperazinyl]phenyl]-2-[(1S,2S)-1-ethyl-2 hydroxypropyl]-2,4-dihydro-3H-1,2,4-triazol-3-one of the structural formula (IV)

| Characteristic Physico-Chemical Data of Amorphous Form of the Compound of Structural Formula IV | |
|---|---|
| Physical appearance: | Off-white to white solid |
| X-ray Powder Diffraction Pattern: | See FIG. 6 |
| DSC: | See FIG. 7 |

Example-8: Preparation of 4-[4-[4-[4-[[(3R,5R)-5-(2,4-difluorophenyl)tetrahydro-5(1H-1,2,4-triazol-1-ylmethyl)-3-furanyl]methoxy]phenyl]-1-piperazinyl]phenyl]-2-[(1S,2S)-1-ethyl-2-hydroxypropyl]-2,4-dihydro-3H-1,2,4-triazol-3-one of the Structural Formula (IV) of Amorphous Form 4-(4-(4-(4-(((3R,5R)-5-((1H-1,2,4-triazol-1-yl)methyl)-5-(2,4-difluorophenyl)tetrahydrofuran-3-yl)methoxy)phenyl)piperazin-1-yl)phenyl)-1-((2S,3S)-2-(benzyloxy)pentan-3-yl)-1H-1,2,4-triazol-5(4H)-one of the structural formula (III) (10.0 g) of crystalline form B-3 was charged to a RBF containing Concentrated Hydrochloric Acid (5.0 vol.) at 25±2° C. The reaction mixture was slowly heated to 62±2° C. and stirred at 62±2° C. for 2 to 3 h. Reaction mass was cooled to 25±2° C. and Dichloromethane (5.0 vol.×2 times) was charged, stirred for 30 minutes and layers were separated. The aqueous layer was added dichloromethane (6.0 vol.) and water (5.0 vol.). The contents were cooled to 15±5° C., pH of the above mass was adjusted to 9 to 10 pH using 25% aqueous sodium hydroxide. Layers were separated. The aqueous layer was re-extracted with dichloromethane (5.0 vol.×2 times). Combined dichloromethane layers were washed with 10% aqueous sodium hydroxide (5.0 vol.×2 times), followed by water (5.0 vol.). Dichloromethane layer was dried over anhydrous sodium sulphate and concentrated the dichloromethane layer under vacuum at 43±2° C. up to 3.0 volume stage. Acetone (4.0 vol.) was added to the reaction mass. This reaction mass was added dropwise to Cyclohexane (20.0 vol.) at 25±2° C. with constant stirring and was continued to stir at the same temperature after addition for 1 hour. Filtered and washed with Cyclohexane (5.0 vol.) and suck dried; dried in VTD at 70±2° C. for 30 to 40 h under vacuum to yield 4-[4-[4-[4-[[(3R,5R)-5-(2,4-difluorophenyl)tetrahydro-5(1H-1,2,4-triazol-1-ylmethyl)-3-furanyl]methoxy]phenyl]-1-piperazinyl]phenyl]-2-[(1S,2S)-1-ethyl-2-hydroxy propyl]-2,4-dihydro-3H-1,2,4-triazol-3-one of the structural formula (IV) of amorphous form with 90% yield.

Example-9: Preparation of 4-[4-[4-[4-[[(3R,5R)-5-(2,4-difluorophenyl)tetrahydro-5(1H-1,2,4-triazol-1-ylmethyl)-3-furanyl]methoxy]phenyl]-1-piperazinyl]phenyl]-2-[(1S,2S)-1-ethyl-2-hydroxypropyl]-2,4-dihydro-3H-1,2,4-triazol-3-one of the Structural Formula (IV) of Amorphous Form 4-(4-(4-(4-(((3R,5R)-5-((1H-1,2,4-triazol-1-yl)methyl)-5-(2,4-difluorophenyl)tetrahydrofuran-3-yl)methoxy)phenyl)piperazin-1-yl)phenyl)-1-((2S,3S)-2-(benzyloxy)pentan-3-yl)-1H-1,2,4-triazol-5(4H)-one of the structural formula (III) (10.0 g) of crystalline form B-3 was charged to a RBF containing Concentrated Hydrochloric Acid (5.0 vol.) at 25±2° C. The reaction mixture was slowly heated to 62±2° C. and stirred at 62±2° C. for 2 to 3 h. Reaction mass was cooled to 25±2° C. and Dichloromethane (5.0 vol.×2 times) was charged, stirred for 30 minutes and layers were separated. The aqueous layer was added dichloromethane (6.0 vol.) and water (5.0 vol.). The contents were cooled to 15±5° C., pH of the above mass was adjusted to 9 to 10 pH using 25% aqueous sodium hydroxide. Layers were separated. The aqueous layer was re-extracted with methylene dichloride (5.0 vol.×2 times). Combined dichloromethane layers were washed with 10% aqueous sodium hydroxide (5.0 vol.×2 times), followed by water (5.0 vol.). Dichloromethane layer was dried over anhydrous sodium sulphate and concentrated the dichloromethane layer under vacuum at 43±2° C. up to 3.0 volume stage. This reaction mass was added dropwise to Cyclohexane (20.0 vol.) at 23±2° C. with constant stirring and was continued to stir at the same temperature for 1 hour. Filtered and washed with Cyclohexane (5.0 vol.) and suck dried; dried in VTD at 70±2° C. for 30 to 40 h under vacuum to yield 4-[4-[4-[4-[[(3R,5R)-5-(2,4-difluorophenyl)tetrahydro-5(1H-1,2,4-triazol-1-ylmethyl)-3-furanyl]methoxy]phenyl]-1-piperazinyl]phenyl]-2-[(1S,2S)-1-ethyl-2-hydroxy propyl]-2,4-dihydro-3H-1,2,4-triazol-3-one of the structural formula (IV) of amorphous form with 92% yield.

The invention claimed is:

1. A process for preparation of crystalline B-3 form of 4-(4-(4-(4-(((3R,5R)-5-((1H-1,2,4-triazol-1-yl)methyl)-5-(2,4-difluorophenyl)tetrahydrofuran-3-yl)methoxy)phenyl)piperazin-1-yl)phenyl)-1-((2S,3S)-2-(benzyloxy)pentan-3-yl)-1H-1,2,4-triazol-5(4H)-one (III) comprising of:
   a) Treating a solution of 1-((2S,3S)-2-(benzyloxy)pentan-3-yl)-4-(4-(4-(4-hydroxyphenyl)piperazin-1-yl)phenyl)-1H-1,2,4-triazol-5(4H)-one (II) in a polar organic solvent under nitrogen atmosphere with an alkali solution at a lower temperature;
   b) Adding ((3S,5R)-5-((1H-1,2,4-triazol-1-yl)methyl)-5-(2,4-difluorophenyl) tetrahydrofuran-3-yl)methyl 4-methylbenzenesulfonate (I) to step a) solution;
   c) Adding an aliphatic ester solvent and water to the solution of step b);
   d) Separating the layers;
   e) Partially concentrating the organic layer and adding an aliphatic hydrocarbon solvent at a lower temperature;
   f) Stirring the reaction mass of step e) at elevated temperature; and
   g) Cooling the reaction mass of step f), filtering and optionally washing with aliphatic hydrocarbon solvent to provide compound III in crystalline Form B-3.

2. A process for preparation of crystalline B-3 form of 4-(4-(4-(4-(((3R,5R)-5-((1H-1,2,4-triazol-1-yl)methyl)-5-(2,4-difluorophenyl)tetrahydrofuran-3-yl)methoxy)phenyl)piperazin-1-yl)phenyl)-1-((2S,3S)-2-(benzyloxy)pentan-3-yl)-1H-1,2,4-triazol-5(4H)-one (III) as claimed in claim 1 comprising of:
   a) Treating a solution of 1-((2S,3S)-2-(benzyloxy)pentan-3-yl)-4-(4-(4-(4-hydroxyphenyl)piperazin-1-yl)phenyl)-1H-1,2,4-triazol-5(4H)-one (II) in dimethyl sulfoxide under nitrogen atmosphere with sodium hydroxide solution at 10-20° C.;
   b) Adding ((3S,5R)-5-((1H-1,2,4-triazol-1-yl)methyl)-5-(2,4-difluorophenyl) tetrahydrofuran-3-yl)methyl 4-methylbenzenesulfonate (I) to step a) solution;
   c) Adding ethyl acetate and water to the solution of step b);
   d) Separating the layers;
   e) Partially concentrating the organic layer to 4-7 volumes and adding n-Heptane at 20 to 30° C.;
   f) Stirring the reaction mass of step e) at 40 to 50° C.; and
   g) Cooling the reaction mass of step f), filtering and optionally washing with n-Heptane to provide compound of the structural formula III in crystalline Form B-3.

3. A crystalline B-3 form of 4-(4-(4-(4-(((3R,5R)-5-((1H-1,2,4-triazol-1-yl)methyl)-5-(2,4-difluorophenyl)tetrahydrofuran-3-yl)methoxy)phenyl) piperazin-1-yl)phenyl)-1-((2S,3S)-2-(benzyloxy)pentan-3-yl)-1H-1,2,4-triazol-5(4H)-one (III) characterized by its powder X-ray diffractogram having peaks at about 7.07, 14.49, 15.68, 16.50, 18.05, 20.13, 20.87, 22.85 and 24.42±0.2 degrees of 2θ.

4. A crystalline B-3 form of 4-(4-(4-(4-(((3R,5R)-5-((1H-1,2,4-triazol-1-yl)methyl)-5-(2,4-difluorophenyl)tetrahydrofuran-3-yl)methoxy)phenyl) piperazin-1-yl)phenyl)-1-((2S,3S)-2-(benzyloxy)pentan-3-yl)-1H-1,2,4-triazol-5(4H)-one (III) as claimed in claim 3 characterized by a XRD pattern as depicted in FIG. 3.

5. A process for preparation of crystalline B-1 form of 4-(4-(4-(4-(((3R,5R)-5-((1H-1,2,4-triazol-1-yl)methyl)-5-(2,4-difluorophenyl)tetrahydrofuran-3-yl)methoxy)phenyl)piperazin-1-yl)phenyl)-1-((2S,3S)-2-(benzyloxy)pentan-3-yl)-1H-1,2,4-triazol-5(4H)-one (III) comprising of:
   a) Treating a solution of 1-((2S,3S)-2-(benzyloxy)pentan-3-yl)-4-(4-(4-(4-hydroxyphenyl)piperazin-1-yl)phenyl)-1H-1,2,4-triazol-5(4H)-one (II) in a polar organic solvent with an alkali solution at a lower temperature;
   b) Adding ((3S,5R)-5-((1H-1,2,4-triazol-1-yl)methyl)-5-(2,4-difluorophenyl) tetrahydrofuran-3-yl)methyl 4-methylbenzenesulfonate (I) to step a) solution;
   c) Adding an aliphatic ester solvent and water to the solution of step b);
   d) Separating the layers;
   e) Concentrating the organic layer and adding a halogenated hydrocarbon solvent and an aliphatic hydrocarbon solvent at a lower temperature; and
   f) Cooling the reaction mass of step e), filtering and optionally washing with aliphatic hydrocarbon solvent to provide compound of the structural formula III in crystalline Form B-1.

6. A process for preparation of crystalline B-1 form of 4-(4-(4-(4-(((3R,5R)-5-((1H-1,2,4-triazol-1-yl)methyl)-5-(2,4-difluorophenyl)tetrahydrofuran-3-yl)methoxy)phenyl)piperazin-1-yl)phenyl)-1-((2S,3S)-2-(benzyloxy)pentan-3-yl)-1H-1,2,4-triazol-5(4H)-one (III) as claimed in claim 5 comprising of:
   a) Treating a solution of 1-((2S,3S)-2-(benzyloxy)pentan-3-yl)-4-(4-(4-(4-hydroxyphenyl)piperazin-1-yl)phenyl)-1H-1,2,4-triazol-5(4H)-one (II) in dimethyl sulfoxide with sodium hydroxide solution at 5-15° C.;

b) Adding ((3 S,5R)-5-((1H-1,2,4-triazol-1-yl)methyl)-5-(2,4-difluorophenyl) tetrahydrofuran-3-yl)methyl 4-methylbenzenesulfonate (I) to step a) solution;
c) Adding ethyl acetate and water to the solution of step b);
d) Separating the layers;
e) Concentrating the organic layer and adding dichloromethane and n-Heptane solvent at a lower temperature; and
f) Cooling the reaction mass of step e), filtering and optionally washing with n-Heptane to provide compound of the structural formula III in crystalline Form B-1.

7. A crystalline B-1 form of 4-(4-(4-(4-(((3R,5R)-5-((1H-1,2,4-triazol-1-yl)methyl)-5-(2,4-difluorophenyl)tetrahydrofuran-3-yl)methoxy)phenyl) piperazin-1-yl)phenyl)-1-((2S,3S)-2-(benzyloxy)pentan-3-yl)-1H-1,2,4-triazol-5 (4H)-one (III) characterized by its powder X-ray diffractogram having peaks at about 4.14, 6.85, 9.92, 15.28, 15.69, 16.59, 17.29, 17.92, 18.27, 18.91, 20.63, 19.95, 23.58 and 25.12±0.2 degrees of 2θ.

8. A crystalline B-1 form of 4-(4-(4-(4-(((3R,5R)-5-((1H-1,2,4-triazol-1-yl)methyl)-5-(2,4-difluorophenyl)tetrahydrofuran-3-yl)methoxy)phenyl) piperazin-1-yl)phenyl)-1-((2S,3S)-2-(benzyloxy)pentan-3-yl)-1H-1,2,4-triazol-5 (4H)-one (III) as claimed in claim 7 characterized by a XRD pattern as depicted in FIG. 1.

9. A process for preparation of crystalline B-2 form of 4-(4-(4-(4-(((3R,5R)-5-((1H-1,2,4-triazol-1-yl)methyl)-5-(2,4-difluorophenyl)tetrahydrofuran-3-yl)methoxy)phenyl) piperazin-1-yl)phenyl)-1-((2S,3S)-2-(benzyloxy)pentan-3-yl)-1H-1,2,4-triazol-5(4H)-one (III) comprising of:
a) Treating a solution of 1-((2S,3S)-2-(benzyloxy)pentan-3-yl)-4-(4-(4-(4-hydroxyphenyl)piperazin-1-yl)phenyl)-1H-1,2,4-triazol-5(4H)-one (II) in a polar organic solvent with an alkali solution at a lower temperature;
b) Adding ((3S,5R)-5-((1H-1,2,4-triazol-1-yl)methyl)-5-(2,4-difluorophenyl) tetrahydrofuran-3-yl)methyl 4-methylbenzenesulfonate (I) to step a) solution;
c) Adding an aliphatic ester solvent and water to the solution of step b);
d) Separating the layers;
e) Partially concentrating the organic layer and adding an aliphatic hydrocarbon solvent at a lower temperature;
f) Stirring the reaction mass of step e) at elevated temperature; and
g) Cooling the reaction mass of step f), filtering and optionally washing with aliphatic hydrocarbon solvent to provide compound of the structural formula III in crystalline Form B-2.

10. A process for preparation of crystalline B-2 form of 4-(4-(4-(4-(((3R,5R)-5-((1H-1,2,4-triazol-1-yl)methyl)-5-(2,4-difluorophenyl)tetrahydrofuran-3-yl)methoxy)phenyl) piperazin-1-yl)phenyl)-1-((2S,3S)-2-(benzyloxy)pentan-3-yl)-1H-1,2,4-triazol-5(4H)-one (III) as claimed in claim 9 comprising of:
a) Treating a solution of 1-((2S,3S)-2-(benzyloxy)pentan-3-yl)-4-(4-(4-(4-hydroxyphenyl)piperazin-1-yl)phenyl)-1H-1,2,4-triazol-5(4H)-one (II) in dimethyl sulfoxide with sodium hydroxide solution at a lower temperature;
b) Adding ((3S,5R)-5-((1H-1,2,4-triazol-1-yl)methyl)-5-(2,4-difluorophenyl) tetrahydrofuran-3-yl)methyl 4-methylbenzenesulfonate (I) to step a) solution;
c) Adding ethyl acetate and water to the solution of step b);
d) Separating the layers;
e) Partially concentrating the organic layer 2-4 volumes and adding heptane at 25 to 30° C.;
f) Stirring the reaction mass of step e) at 40 to 50° C.; and
g) Cooling the reaction mass of step f), filtering and optionally washing with heptane to provide compound of the structural formula III in crystalline Form B-2.

11. A crystalline B-2 form of 4-(4-(4-(4-(((3R,5R)-5-((1H-1,2,4-triazol-1-yl)methyl)-5-(2,4-difluorophenyl)tetrahydrofuran-3-yl)methoxy)phenyl) piperazin-1-yl)phenyl)-1-((2S,3S)-2-(benzyloxy)pentan-3-yl)-1H-1,2,4-triazol-5 (4H)-one (III) characterized by its powder X-ray diffractogram having peaks at about 4.20, 9.27, 14.22, 15.46, 15.82, 16.45, 17.31, 19.09, 20.47, 21.18 and 24.74±0.2 degrees of 2θ.

12. A crystalline B-2 form of 4-(4-(4-(4-(((3R,5R)-5-((1H-1,2,4-triazol-1-yl)methyl)-5-(2,4-difluorophenyl)tetrahydrofuran-3-yl)methoxy)phenyl) piperazin-1-yl)phenyl)-1-((2S,3S)-2-(benzyloxy)pentan-3-yl)-1H-1,2,4-triazol-5 (4H)-one (III) as claimed in claim 11 characterized by a XRD pattern as depicted in FIG. 2.

* * * * *